United States Patent [19]
Esteras et al.

[11] Patent Number: 5,962,421
[45] Date of Patent: Oct. 5, 1999

[54] PHARMACOLOGICAL ASSOCIATION BETWEEN N-ACETYLCYSTEINE AND LEVULOSE FOR PREVENTING CELLULAR DEATH AND RELATED DISEASES

[75] Inventors: Antonio Esteras; Leonida Bruseguini, both of Barcelona; José Maria Estrela, Valencia, all of Spain

[73] Assignee: Zambon, S.A., Santa Perpetua de Mogoda, Spain

[21] Appl. No.: 09/007,071

[22] Filed: Jan. 14, 1998

Related U.S. Application Data

[63] Continuation of application No. PCT/ES97/00122, May 13, 1997.

[51] Int. Cl.⁶ .................. A61K 31/70; A61K 31/195
[52] U.S. Cl. ................................ 514/23; 514/562
[58] Field of Search ........................ 514/23, 562

[56] References Cited

U.S. PATENT DOCUMENTS

| | | | |
|---|---|---|---|
| 4,970,236 | 11/1990 | Ziggiotti et al. | 514/562 |
| 5,292,538 | 3/1994 | Paul et al. | 426/74 |

FOREIGN PATENT DOCUMENTS

| | | |
|---|---|---|
| 339508 | 11/1989 | European Pat. Off. . |
| 9307857 | 4/1993 | WIPO . |
| 9402036 | 2/1994 | WIPO . |

OTHER PUBLICATIONS

Kaneto et al., *Biochemical Journal*, vol. 320 (Pt. 3) : 855–863, (Dec. 15, 1996).

*Primary Examiner*—Howard C. Lee
*Attorney, Agent, or Firm*—Henderson & Sturm

[57] ABSTRACT

A method for prevention of cell death, and method comprising simultaneously topically applying N-acetylcysteine and levulose as an application in an amount effective to result in a synergistic action protecting cells, and preventing cell damage caused by various agents. A method of preparing pharmaceutical compounds that protect cells against damage induced by a member selected from the group consisting of hypoxia/anoxia, oxidative stress, xenobiotic agents, ionizing radiations, and conditions causing toxic stress, which involves forming a combination comprising N-acetylcysteine and levulose. A pharmaceutical preparation including a combination of N-acetylcysteine and levulose.

9 Claims, No Drawings

PHARMACOLOGICAL ASSOCIATION BETWEEN N-ACETYLCYSTEINE AND LEVULOSE FOR PREVENTING CELLULAR DEATH AND RELATED DISEASES

CROSS-REFERENCE TO RELATED APPLICATIONS

This is a Continuation under 35 U.S.C. 120 of International Patent Application No. PCT/ES97/00122, filed May 13, 1997, claiming priority of Spanish Application No. P 9601091, the disclosure of which in its entirety is incorporated by reference thereto herein.

STATEMENT REGARDING FEDERALLY SPONSORED RESEARCH OR DEVELOPMENT

Not Applicable).

AUTHORIZATION PURSUANT TO 37 C.F.R. §1.71 (d) (e)

A portion of the disclosure of this patent document, including appendices, may contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention uses N-acetylcysteine and levulose as cell protectors in the pharmacological therapy of many diseases that are followed by cell death associated with phenomena of oxidative stress.

2. Description of the Related Art

Various groups of scientists recently demonstrated that high concentrations of fructose prevent the anoxic death of hepatic cells. Various mechanisms were suggested to explain this protective effect:

a) an increment of the glycolytic production of lactate, which can directly protect the cells; b) an increased anaerobic synthesis of adenosine-triphosphate (ATP); c) an inhibition of the production of free radicals; d) a modulation of the homeostasis of $Ca^{2+}$. In spite of these hypotheses, however, the molecular mechanisms involved in the protective effect afforded by the fructose are still not explained.

Under anaerobic conditions, levulose is a better glycolytic substrate than glucose or other carbohydrates and produces very high proportions of lactate. Just lactate (10 mH), however, does not prevent the anoxic death of cells. Thus, although lactate may contribute to the low intracellular pH (pH i) found after 30 minutes of anoxia in the presence of levulose, lactate by itself does not explain the protective function carried out by levulose against anoxic damage. The anoxic damage is clearly reduced by lowering the extracellular pH and, therefore, gives rise to an intracellular acidification. However, if the pH i is linked to an extracellular pH of 7.4 because of the use of monensine, which modulates the exchange of Na for H, levulose also protects against cell death. Therefore, both acidosis and levulose can protect against cell death by independent mechanisms.

In aerobic metabolisms, the necessary energy to maintain the cell integrity is supplied by the cytochromic mitochondrial system. In the case of anoxia, the lack of oxygen does not allow the formation of ATP by oxidative phosphorylation and the stored ATP is very quickly consumed. As a matter of fact, the depletion of ATP is a certain fact under hypoxic conditions or those of toxic damages. It is not clear, however, in which manner an ATP deficit becomes an irreversible damage. Levulose has shown to be effective in the protection of hepatocytes of rats against lethal damages caused by mitochondrial inhibitors, such as cyanide, oligomycin or menadione. Some authors suggested that the protective mechanism by levulose should entail the glycolytic production of ATP. Levulose, however, cannot protect the cells against the hypoxic damages by merely maintaining the glycolytic production of ATP.

An increased concentration of the free intracellular $Ca^{2+}$, that can cause the activation of the degrading enzymes dependent on $Ca^{2+}$, such as phospholipase A, endonuclease and protease, generally accompanies the necrosis of the liver. The function of the free intracellular $Ca^{2+}$ in cytotoxicity was especially studied in the hepatocytes. Glutathione (GSH) plays a critical part in the regulating of the sequestrum of $Ca^{2+}$ in the endoplasmic reticulum. Furthermore, under conditions of an increase in the forming of disulfide glutathione (GSSG), e.g., during an oxidative stress, the GSSG is reduced to GSH by the reductase glutathione, at the expense of nicotinamide-adenosine-dinucleotide-phosphate (NADPH). Therefore, the oxidation of GSH may facilitate a change in the amount of mitochondrial $Ca^{2+}$.

Glutathione is always present in the eukaryotic cells and is involved in many cell functions. It is the most prevalent cellular thio and the most abundant peptide of low molecular weight present in the cells. The GSH acts as a reducing agent and as an antioxidant, serves as a reserve of cysteine, participates in reactions of detoxification of xenobiotics and in the metabolism of numerous cell compounds, it is required for the synthesis of some prostaglandins, and it is connected with the regulating of the cell cycle and with thermotolerance. This tripeptide plays a part in the protection against tissular damages resulting from the exposition to oxidant environments such as hyperoxia, hyperbaric oxygen or ozone, and it can also protect against radiations, ultraviolet light and photodynamic effects.

In view of the foregoing, a possible explanation of the protective effect of levulose with respect to the hepatic cell death, under toxic stress conditions, can be summarized in the hypothesis that there might exist a relationship between the maintaining of the levels of the cellular NADPH, the status of glutathione and calcic homeostasis, and the incidence of levulose on these cell phenomena.

On the other hand, various studies have shown the symptomatic amelioration of some diseases, e.g. chronic bronchitis, after treatment with N-acetylcysteine (NAC). In spite of some variations in the efficiency obtained between one and other studies, there are many data that suggest that the NAC can ameliorate the symptoms of chronic bronchitis. The most important improvements observed are with respect to the decrease in the amount and purulence of the sputum, the rate of exacerbation, and/or the number of sick days. Among the well known characteristics of bronchitis, mention must made of: ciliary paralysis, hyperplasia of the mucous cells, obstruction because of mucus, infection, inflammation, and cell lesion (fibrosis). In many instances, the beginning of bronchitis is caused by cigarette smoke. A vicious circle develops as a result of this lesion, that leads to hypoxia, emphysema and, oftentimes, death. From a clinical perspective, data exist that indicate that NAC may reduce the symptoms that weaken patients suffering from chronic bronchitis.

In order to explain the possible mechanisms that cause the symptomatic improvement of patients suffering from chronic bronchitis who had been treated with NAC, it must be taken into account: that on the one hand, it is probable that the mucolytic properties of NAC contribute to the clinical improvement; but that, on the other hand, it may happen that some of the antioxidant properties of NAC are also beneficial for patients suffering from chronic bronchitis. This last supposition is mainly based on the findings that iodoglycerol, a mucolytic not having any antioxidant properties, which reduces in an efficient manner some of the symptoms of bronchitis, does not seem to be as clinically efficient as NAC, which is a mucolytic with antioxidant properties.

Among the oxidative mechanisms that may contribute to the chronic bronchitis, it must be pointed out that, for example, tobacco smoke may alter the oxidant/antioxidant equilibrium in the lungs and that therefore it can influence the development of chronic bronchitis in various manners. Among the various possibilities that can produce alterations in the oxidant/antioxidant equilibrium are: a) an increase in the production or the conversion of xanthine dehydrogenase (XD) to xanthine oxidase (XO), which leads to an increase in the forming of metabolites of oxygen in the pulmonary cells. In turn, the increased oxidative stress can increase the conversion of GSH to oxidized GSH (GSSG), inactivate the antiproteinases and/or bring about cellular hyperplasia. Likewise, tobacco smoke could increase the number and the activity of the alveolar macrophages or neutrophils in the lungs, and increase the release of oxygen radicals by said cells. Further, the oxygen radicals may form chemotaxis which, in turn, can attract more neutrophils. The attracted phagocytes could release more oxidants, as well as elastase, contributing even more to upset in a synergetic manner the oxidants/antioxidants equilibrium and to cause cell lesions.

Various studies conducted by different authors to examine the effect of NAC on the oxidants/antioxidants equilibrium revealed:

The alveolar macrophages (MA) obtained through the washing of the lungs of asymptotic cigarette smokers produce more superoxide anion in vitro than the MA of the lungs of healthy control individuals.

The adjunction of neutrophils stimulated with forbol myristic acetate (PMA) produced lesions of the pulmonary epithelial cells cultivated in vitro, which is reflected by the release of $Cr^{51}$ pre-incorporated into the epithelial cells. The treatment with NAC protected to a considerable extent against the lesion caused by neutrophils.

The release of superoxide anion by the MA of cigarette smokers is reduced in the individuals who took NAC during an 8-week period.

The number of cells of the high and low airways of rats exposed to cigarette smoke was reduced with NAC treatment.

It can be definitively asserted that the oxidants/antioxidants equilibrium is a key element in many diseases, among them, chronic bronchitis.

A summary of the factors producing oxidant lesions and of those providing antioxidant defenses can be as follows:

Oxidant lesions are produced by:

XO

Phagocytes

Mitochondrias

AA metabolism

Environmental pollution

Tobacco

Antioxidant defenses are:

SOD (dismutase superoxide)

Catalase

Vitamin E

Ceruloplasmin

Redux reactions of the glutathione

NAC seems to possess the capacity of tilting the equilibrium in favor of the antioxidants, possibly acting as an efficient agonist of the GSH.

Those concerned with these and other problems recognize the need for an improved method in accordance with the present invention.

BRIEF SUMMARY OF THE INVENTION

The present invention intended to be claimed is described herein.

The present invention is directed to a method for prevention of cell death which involves simultaneously topically applying N-acetylcysteine (NAC) and levulose as an application in an amount effective to result in a synergistic action protecting cells, and preventing cell damage caused by various agents, wherein the N-acetylcysteine and the levulose are present in (the application in a proportion comprising a molar ratio between about of 1/1 to 5/1, and most preferably wherein said molar ratio is 4/1.

The present invention is also directed to a method which involves forming a combination comprising N-acetylcysteine and levulose in amounts effective to result in a strong synergistic effect that gives rise to a strong antioxidant action of a cell, wherein the N-acetylcysteine and the levulose are present in a proportion comprising a molar ratio of 1/1 to 5/1.

The present invention is also directed to a method of preparing pharmaceutical compounds that protect cells against damage induced by a member selected from the group consisting of hypoxia/anoxia, oxidative stress, xenobiotic agents, ionizing radiations, and conditions causing toxic stress, which involves forming a combination comprising N-acetylcysteine and levulose.

The present invention is also directed to a pharmaceutical preparation comprising a combination of N-acetylcysteine and levulose, wherein the N-acetylcysteine and the levulose are present in a proportion comprising a molar ratio of 1/1 to 5/1.

Having reviewed all of the foregoing regarding the favorable effects separately presented by levulose and N-acetylcysteine for the maintaining of the cells, we have recently proven, and the objective of the present invention is based thereupon, that the combination of levulose with N-acetylcysteine presents a strong synergistic protective effect against oxidative stress in isolated hepatocytes of rats.

It was proven that the levulose and NAC combination protects the hepatic cells against cell death induced by tertbutyl-hydroperoxide (t-Bu-OOH). None of these two products, when administered by itself, can reach the high degree of cell protection obtained by the combination described in the present invention. Also other known hepatoprotectors, such as methionine, S-adenosil-methionine or arginine-thiazolidine-carboxylate cannot protect against the damage caused by strong oxidants to the hepatic cells.

In view of all the foregoing, the objective of the present invention is a pharmacological combination that protects cells against different toxins or stress conditions of the cells.

The objective of the present invention is the combination of N-acetylcysteine and levulose as a protector against the damages caused by hypoxia/anoxia, oxidative stress, different xenobiotics, and ionizing radiations.

Another objective of the invention is the use of the NAC and levulose combination for the preservation of the mitochondrial cell functions (membrane potential, oxidative phosphorylation, etc.).

Another objective of the present invention is the use of the NAC-levulose combination for the preparation of a pharmaceutical compound that protects the cells against different toxins or stress conditions of the cells.

Lastly, another objective of the present invention is a pharmaceutical compound having as active component a NAC and levulose combination.

For a therapeutical application, the NAC-levulose combination is preferably incorporated into a pharmaceutical compound for oral or parenteral administration.

Depending on the chosen administration, the compounds in accordance with the present invention can be in the form of tablets, capsules, pills, and the like, or in the form of a liquid preparation of easy use or to be prepared by dilution at the moment of use.

The compounds may contain the NAC-levulose combination with pharmaceutically accepted carriers, that can be solids or liquids, organic or inorganic pharmaceutical excipients, such as disintegrating or diluent agents, or the like.

In addition to the excipients, the compounds may contain preservatives, stabilizers, humectants, tampons, stains, and flavorings.

DETAILED DESCRIPTION OF THE INVENTION

The present invention is directed to a method for prevention of cell death, which involves simultaneously topically applying N-acetylcysteine and levulose as an application in an amount effective to result in a synergistic action protecting cells, and preventing cell damage caused by various agents, wherein the N-acetylcysteine and the levulose are present in the application in a proportion comprising a molar ratio between about of 1/1 to 5/1, and most preferably, wherein the molar ratio is 4/1.

The present invention is also directed to a method which involves forming a combination comprising N-acetylcysteine and levulose in amounts effective to result in a strong synergistic effect that gives rise to a strong antioxidant action of a cell, wherein the N-acetylcysteine and the levulose are present in a proportion comprising a molar ratio of 1/1 to 5/1.

The present invention is also directed to a method of preparing pharmaceutical compounds that protect cells against damage induced by a member selected from the group consisting of hypoxia/anoxia, oxidative stress, xenobiotic agents, ionizing radiations, and conditions causing toxic stress, which involves forming a combination comprising N-acetylcysteine and levulose.

The present invention is also directed to a pharmaceutical preparation comprising a combination of N-acetylcysteine and levulose, wherein the N-acetylcysteine and the levulose are present in a proportion comprising a molar ratio of 1/1 to 5/1.

A complete listing of all the pathological entities in which the simultaneous application of the N-acetylcysteine-levulose combination could be directly or indirectly indicated would be very long. Therefore, they are grouped in large sections; reference is made only of some because of their special clinical relevance:

1.—Otorrhinolaryngology: otitis, sinusitis, rhinopharyngitis, laryngotracheitis.

2.—Respiratory system: acute and chronic bronchitis, asthmatic bronchitis, emphysema, bronchoneumonias, pulmonary tuberculosis.

3.—Hepatology: acute and chronic hepatopathies.

4.—Cardiovascular system: myocardial infarctation, arterio- sclerosis, phlebitis, arteritis.

5.—Renal system: nephritis and nephrosis

6.—Nervous system: neurodegenerative diseases, such as Alzheimer's or Parkinson's.

7.—Immunology: as immunostimulant for immunodeficiencies, such as AIDS or for the immunotherapy of cancer.

8.—Oncology: as anticarcinogen and protection of skeletal muscular cells faced with the loss of muscular mass associated with cachexia tumoral.

9.—Sex organ: for male infertility because of affectation of the spermatazoids (oligospermia, decreased motility)

10.—Ophthalmology: retinitis.

11.—Dermatology: degenerative dermatitis (for example, by contact, medicamentous dermatitis), affectations of the pilose follicles (for example, alopecia).

12.—Nuclear medicine: as radioprotector against the cellular lesions derived from the exposition to toxic doses of ionizing radiations.

By way of example, Table 1 shows the protective effect of the NAC-levulose combination with respect to the oxidative stress in isolated hepatocytes of rats. Protective effect of the NAC-levulose combination with respect to the oxidative stress in isolated hepatocytes of rats.

TABLE 1

| Adjunctions | Cellular viability | GSH ($\mu$mol/g) | GSSG (nmol/g) |
|---|---|---|---|
| None | 83 ± 5 | 3.2 ± 0.3 | 221 ± 68 |
| Glucose | 90 ± 2 | 3.5 ± 0.3 | 25 ± 11* |
| Levulose | 91 ± 4 | 3.6 ± 0.4 | 19 ± 10* |
| NAC | 90 ± 2 | 4.6 ± 0.3 | 29 ± 7* |
| Glucose + NAC | 90 ± 5 | 4.7 ± 0.5* | 31 ± 9* |
| Levulose + NAC | 92 ± 3* | 5.2 ± 0.3* | 18 ± 5* |
| t-Bu—OOH | 0 ± 0 | 0 ± 0* | 2978 ± 58* |
| t-Bu—OOH + glucose | 0 ± 0* | 0.1 ± 0.1* | 2869 ± 101* |
| t-Bu—OOH + levulose | 80 ± 7+ | 1.6 ± 0.4← | 1739 ± 259++ |
| t-Bu—OOH + NAC | 0 ± 0* | 0.3 ± 0.1← | 2733 ± 185* |
| t-Bu—OOH + glucose + NAC | 0 ± 0* | 0.4 ± 0.1← | 2671 ± 226* |
| tbOOH + levulose + NAC | 92 ± 3*+ | 4.0 ± 0.4← | 96 ± 3*+ |

The isolated hepatocytes were obtained from Wistar rats (200–250 g; without food for 24 hours) according to the Berry & Friend method (J. Cell Biol., 43; 508–520, 1969). The cells were incubated (10–12 mg of dry weight/ml) at 37° C. in Krebs-Henseleit (pH 7.4) containing 1.3 mM of $CaCl_2$. The gaseous atmosphere consisted of 95% $O_2$–6x$CO_2$. The various substrates were incubated at the following concentrations: glucose, 5 mM; levulose, 2 mM; NAC, 0.5 mM; tert.butyl hydroperoxide (t-Bu-OOH), 1 mM. The incubation period was of 60 minutes. The control values at "zero time" are as follows: cellular viability (%): 92±2; GSH ($\mu$mol/g): 3.5±0.3; GSSG (nmol/g): 52±13.

As shown by the results, the combination of NAC and levulose, with application of both, has a very strong effect. The cells that are exposed to the action of a high concentration of terbutyl-hydro-peroxide (1 mM) die because of cell necrosis within a period of less than 30 minutes. The incubation period of the tests of Table 1 was of 60 minutes in order to be able to observe the effects over a somewhat longer period of time.

The results indicate that the NAC (0.5 mM) and levulose (2 mM) combination completely prevents the death by oxidation. None of the two molecules, separately, can prevent cellular stress as shown by the GSSG values, that are an excellent index of oxidative stress.

Levulose, in the absence of NAC, reduces to a great extent the GSH oxidation and prevents, at short term, the cell necrosis. However, the combination of NAC+levulose is necessary to prove total protection to the cells, either by using the mentioned proportion of levulose/NAC=2/0.5 or by using other proportions of roughly this ratio.

The effect that is observed when incubating levulose by itself is probably due to the synthesis of NADPH, a cofactor that intervenes in the decrease of the GSSG through reductase glutathione. However, the partial effect of levulose does not prevent the cumulative cell damage, a consequence of having suffered an oxidative stress. This is the reason for which the cellular viability gradually diminishes until suddenly dropping if the intracellular levels of GSH are very low. NAC, as an ideal precursor of the GSH synthesis, raises the content of tripeptides to physiological levels.

It is very important to take into account that the parameter "cellular viability" (of Table 1) only indicates if a cell is alive or dead, and whether accumulated molecular damages exist as a consequence of the exposition to the oxidative stress. Accumulated damages that reduce the metabolic functions of the affected cells and their mid- and long term survival. Therefrom results that the redox state of the glutathione, that is indicative of the cell damage due to oxidation, evidence more clearly the synergetic protective effect of the combination NAC-levulose.

EXAMPLES

The present invention, objective of this patent, can be industrially used in the manufacture and marketing of pharmaceutical specialties. The following are not limitative examples:

| AMPOULES Medicinal substance | |
|---|---|
| Acetylcysteine | 300.0 mg |
| Levulose | 500.0 mg |
| Excipient(s) | |
| Sodium ecetate | 3.0 mg |
| Sodium hydroxyl | 73.0 mg |
| Water for injection | 3.0 ml |
| INJECTABLE SOLUTION FOR PERFUSIONS Active ingredients | |
| Acetylcysteine | 2.0 mg |
| Levulose | 4.0 mg |
| Excipients | |
| Bisodium ecetate | 0.02 g |
| Sodium hydroxyl c.s.p. pH = | 5.50 |
| Water for injection c.s.p. | 10.00 ml |
| ENVELOPES Medicinal substance | |
| Acetylcysteine | 0.20 g |
| Levulose | 0.400 |
| Excipient(s) | |
| Orange granulate | 0.500 g |
| Saccharine | 0.008 g |
| Orange fragrance | 0.050 g |
| Yellow [sunset] stain (E-110) | 0.001 g |
| Saccharose c.s.p. | 5.000 g |
| CHILDREN'S ENVELOPES Medicinal substance | |
| Acetylcysteine | 0.100 g |
| Levulose | 0.200 |
| Excipient(s) | |
| Orange granulate | 0.500 g |
| Saccharine | 0.008 g |
| Orange fragrance | 0.050 g |
| Yellow [sunset] stain (E-110) | 0.001 g |
| Saccharose c.s.p. | 5.000 g |
| EFFERVESCENT TABLETS Active ingredients | |
| N-acetylcysteine | 600 mg |
| Levulose | 1200 mg |
| Excipient(s) | |
| Sodium bicarbonate | 500 mg |
| Citric acid | 680 mg |
| Aspartaine | 20 mg |
| Lemon fragrance | 100 mg |

In connection with antibiotics, the synergism between NAC and levulose may be used in the therapy of infectious diseases.

EXAMPLES

The following are not limitative examples:

| AMPOULES Active ingredients | |
|---|---|
| Levogyre thiamphenycol | 250.0 mg |
| Acetylcysteine | 113.0 mg |
| Levulose | 226.0 mg |
| Excipient(s) | |
| Talc | 2.5 mg |
| Magnesium stearate | 2.5 mg |
| LYOPHILIZED VIALS Medicinal substance | |
| Thiamphenycol glycinate acetylcysteinate (equivalent to thiamphenycol and acetycycsteine | 405 mg 250 mg 113 mg |
| Levulose | 226 mg |
| Excipient(s) (by ampoule of dissolvent) | |
| Bisodium ecetate | 1.25 mg |
| Water for injection c.s.p. | 2.00 ml |
| STRONG LYOPHILIZED VIAL Medicinal substance | |
| Thiamphenycol glycinate acetylcysteinate (equivalent to thiamphenycol and acetylcysteine | 1,215 mg 750 mg 339 mg |
| Levulose | 678 mg |
| Excipient(s) (by ampoule of dissolvent) | |
| Bisodium ecetate | 3.75 mg |
| Water for injection c.s.p. | 400 mg |
| ENVELOPES Active ingredients | |
| Amoxicillin trihidrate (equivalent to amoxicillin anhydrous) | 287.0 mg 250.0 mg |
| N-acetylcysteine | 100.0 mg |

-continued

| | |
|---|---|
| Levulose | 200.0 mg |
| Excipients | |
| Sodic carboxymethylcellulose | 50.0 mg |
| Orange fragrance | 100.0 mg |
| Acid saccharine | 4.0 mg |
| E 110 stain (orange A-1) | 0.8 mg |
| Ethylcellulose | 11.6 mg |
| Saccharose c.s.p. | 5 g |
| ENVELOPES | |
| Active ingredients | |
| Amoxicillin trihidrate | 574.000 mg |
| Microencapsulated acetylcystein | 222.200 mg |
| Levulose | 444.400 mg |
| Excipients | |
| Orange fragrance | 100.000 mg |
| Sodic carboxymethylcellulose | 50.000 mg |
| Acid saccharine | 8.000 mg |
| Orange A-1 stain | 0.800 mg |
| Sieved saccharose | 4,045.000 g |

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

What is claimed is:

1. A method for prevention of cell death, said method comprising simultaneously administering N-acetylcysteine and levulose as an application in an amount effective to result in protecting cells, and preventing cell damage caused by various agents.

2. A method in accordance with claim 1, wherein said N-acetylcysteine and said levulose are present in said application in a proportion comprising a molar ratio between about of 1/1 to 5/1.

3. A method in accordance with claim 2, wherein said molar ratio is 4/1.

4. A method in accordance with claim 1, wherein said application comprises N-acetylcysteine and levulose in amounts effective to result in antioxidant action of a cell.

5. A method in accordance with claim 4, wherein said N-acetylcysteine and said levulose are present in a proportion comprising a molar ratio of 1/1 to 5/1.

6. A method of preparing pharmaceutical compounds that protect cells against damage induced by a member selected from the group consisting of hypoxia/anoxia, oxidative stress, xenobiotic agents, ionizing radiations, and conditions causing toxic stress, said method comprising forming a combination comprising N-acetylcysteine and levulose wherein said N-acetylcysteine and said levulose are present in a proportion comprising a molar ratio of 1/1 to 5/1.

7. A method of forming a pharmaceutical preparation, said method comprising: forming a combination comprising N-acetylcysteine and levulose in amounts effective to result in antioxidant action of a cell, wherein said N-acetylcysteine and said levulose are present in a proposition comprising a molar ratio of 1/1 to 5/1.

8. A pharmaceutical preparation produced in accordance with claim 7.

9. A pharmaceutical preparation comprising a combination of N-acetylcysteine and levulose, wherein said N-acetylcysteine and said levulose are present in a proportion comprising a molar ratio of 1/1 to 5/1.

* * * * *